(12) United States Patent
Bergin et al.

(10) Patent No.: US 9,421,093 B2
(45) Date of Patent: Aug. 23, 2016

(54) VALVE HOLDER

(75) Inventors: Cathy A. Bergin, Brooklyn Park, MN (US); Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 945 days.

(21) Appl. No.: 13/249,944

(22) Filed: Sep. 30, 2011

(65) Prior Publication Data

US 2012/0022641 A1    Jan. 26, 2012

Related U.S. Application Data

(62) Division of application No. 11/357,224, filed on Feb. 17, 2006, now Pat. No. 8,057,538.

(60) Provisional application No. 60/654,116, filed on Feb. 18, 2005.

(51) Int. Cl.
*A61F 2/24* (2006.01)

(52) U.S. Cl.
CPC ............ *A61F 2/2409* (2013.01); *A61F 2/2427* (2013.01); *A61F 2/2412* (2013.01); *A61F 2250/0097* (2013.01)

(58) Field of Classification Search
CPC ........... A61F 2/24; A61F 2/04; A61F 2/2409; A61F 2/2427; A61F 2/2412; A61F 2250/0097
USPC ..................... 623/2.1–2.42; 81/467; 606/139, 606/144–148
See application file for complete search history.

(56) References Cited

U.S. PATENT DOCUMENTS

| | | |
|---|---|---|
| 4,211,325 A | 7/1980 | Wright |
| 4,865,600 A | 9/1989 | Carpentier et al. |
| 5,443,502 A | 8/1995 | Caudillo et al. |
| 5,476,510 A | 12/1995 | Eberhardt et al. |
| 5,480,425 A | 1/1996 | Ogilive |
| 5,549,665 A | 8/1996 | Vesely et al. |
| 5,662,704 A * | 9/1997 | Gross ............................. 623/2.1 |
| 5,716,401 A | 2/1998 | Eberhardt et al. |
| 5,776,187 A | 7/1998 | Krueger et al. |
| 6,126,007 A | 10/2000 | Kari et al. |
| 6,338,740 B1 | 1/2002 | Carpentier |
| 6,409,758 B2 | 6/2002 | Stobie et al. |
| 6,558,418 B2 | 5/2003 | Carpentier et al. |
| 6,645,244 B2 | 11/2003 | Shu et al. |

(Continued)

FOREIGN PATENT DOCUMENTS

| | | |
|---|---|---|
| GB | 2011259 | 7/1979 |
| GB | 2 108 393 | * 5/1983 |
| GB | 2108393 | 5/1983 |

*Primary Examiner* — Victor Nguyen (57) ABSTRACT

Methods and apparatus for holding and maneuvering a valve during preparation and attachment to patient, providing increased visibility of the prosthetic valve and the sewing ring to prevent suture entanglement. A handle attachment is spaced from the valve for improved visibility of the sewing ring and the outlet end of the valve during attachment. Commissure posts are bent inward at the tips while preventing crashing of the commissure posts into each other causing damage. A release force needed to remove the holder and unthread the holder sutures is reduced. The holder and related methods can provide a kink free holder suture path to reduce suture entanglement and prevent damage to the implanted valve during holder removal by reducing the release force needed to remove the holder sutures by up to 30%.

13 Claims, 11 Drawing Sheets

(56) References Cited

U.S. PATENT DOCUMENTS

| | | |
|---|---|---|
| 6,702,852 B2 | 3/2004 | Stobie et al. |
| 6,736,845 B2 * | 5/2004 | Marquez et al. ............. 623/2.11 |
| 6,893,459 B1 | 5/2005 | MacOviak |
| 6,964,682 B2 | 11/2005 | Nguyen-Thien-Nhon et al. |
| 6,966,925 B2 | 11/2005 | Stobie |
| 2002/0082686 A1 | 6/2002 | Nguyen-Thien-Nhon et al. |
| 2003/0125805 A1 * | 7/2003 | Johnson et al. ............... 623/2.11 |
| 2003/0221524 A1 * | 12/2003 | Hu .................................. 81/467 |
| 2004/0024451 A1 * | 2/2004 | Johnson et al. ............... 623/2.11 |
| 2004/0138741 A1 | 7/2004 | Stobie et al. |
| 2004/0148018 A1 | 7/2004 | Carpentier et al. |

* cited by examiner

VALVE HOLDER

CROSS-REFERENCE TO RELATED APPLICATIONS

This application is a divisional of U.S. application Ser. No. 11/357,224, filed Feb. 17, 2006, entitled "Valve Holder" which claims the benefit of U.S. Provisional Application No. 60/654,116, filed Feb. 18, 2005 and entitled "Valve Holder"; the entire teachings of each of which are incorporated herein by reference.

FIELD OF THE INVENTION

The present invention relates to methods used to place prosthetic valves in patients and apparatus used in the methods. More specifically, the present invention relates to tools, apparatus and methods used to hold a heart valve during insertion and attachment during a heart valve replacement procedure.

BACKGROUND

Heart valve replacement is a common procedure for patients suffering from heart valve damage due to a variety of ailments and disease. Prosthetic heart valves comprise two main types, mechanical and natural tissue valves. Mechanical replacement heart valves comprise a mechanical apparatus usually made from metal or plastic having mechanisms to allow flow in one direction and resisting flow in the opposite direction. An example of a mechanical heart valve is described in U.S. Pat. No. 6,645,244 for MECHANICAL HEART VALVE PROSTHESIS to Shu, et al and assigned to the assignee of the present application. In the '244 patent, flow enabling leaflets are supported for pivotal movement in an improved design to wash the hinge recess to increase the life of the valve.

Natural or Biosynthetic heart valves are made by using a tissue valve from a large mammal (porcine, bovine, equine). These natural tissue valves are removed from the animal, and chemically fixed to preserve the tissue to prevent rejection by the patient. The natural tissue valve is usually enhanced with support and attachment devices. The tissue valve comprises movable tissue flaps called leaflets to control the directional flow of blood. An example of a prior art tissue valve is described in U.S. Pat. No. 5,549,665 to Vesley et al. entitled, BIOPROSTETHIC VALVE. In the '665 patent a valve made of natural tissue is mounted on a stent having commissure posts and a sewing ring. The stent is covered with a biocompatible material.

Both mechanical and natural prosthetic valves may use a sewing ring at the inlet of the valve structure and a stent surrounding the valve. The surgeon attaches the valve to the patient by suturing the sewing ring to the annulus of the valve to be replaced. The stunt of a natural prosthetic valve comprises commissure posts extending circumferentially from the sewing ring and around the outlet of the valve. The stent supports tissue around the valve to allow the valve to control the flow of blood. The stent helps the leaflets move by holding surrounding tissue spaced from the valve.

A valve holder is removably connected to the stent or sewing ring to hold the valve during placement in the patient. The physician performing the valve replacement, attaches a handle to the valve holder to remove it from the packaging and prepare for insertion. The valve is held in a position outside the annulus during the initial placing of the valve sutures. The valve may be oriented for optimum performance, for example, aligning the largest inter-commissure space with the right fibrous trigone. The valve sutures are individually threaded onto the annulus of the patient's defective valve and extended to a corresponding position on the outer portion of the sewing ring of the replacement valve. The valve sutures prevent leaking around the sewing ring by close spacing around the entire perimeter of the heart valve. The valve sutures are placed so as to create an orderly array or web connection around the entire valve. Accessibility of the entire circumference of the sewing ring for suture placement is desirable. The physician must be careful to engage only the sewing ring on the prosthetic valve. Suture entanglement with the holder, or the stent creates a loose connection. Furthermore, care must be taken to not entangle or suture the leaflets during the connection process.

The valve sutures must avoid the holder sutures attaching the holder to the sewing ring and especially the knots terminating the holder sutures. Entanglement of the valve sutures with the holder, holder sutures or holder suture knots could cause paravalvular leakage when the holder is removed after the valve has been secured. The connection between the holder and the sewing ring should be isolated from the valve sutures to avoid entanglement.

Thus, visibility of the sewing ring and the leaflets is important during the attachment process. The handle and the holder in prior art designs block visibility along the axis of the valve making suture entanglement difficult to avoid. In attaching a mitral valve for example, the leaflets and stent are distal to the handle and difficult to observe with prior art designs. An example of a prior art holder where visibility is limited is described in U.S. Pat. No. 5,776,187 for COMBINED HOLDER TOOL AND ROTATOR FOR A PROSTHETIC HEART VALVE to Krueger et al. In the '187 patent, a holder is described that partially blocks visibility of the outer portion of the sewing ring and further blocks visibility along the axis of the valve through the sewing ring. Visibility of the sewing ring is critical to assure the sutures are well placed. Visibility past the holder into the area of the leaflets helps the physician avoid entangling the leaflets with the valve sutures. Preferably, the valve leaflet should be visible through the interior of the sewing ring.

In addition to visibility, tissue accessibility is also important. Access to the tissue from both the inflow and outflow sides of the valve allows for irrigation of the tissue to prevent drying during surgery.

It is known in the prior art to draw the commissure posts inward to contain and isolate the leaflets during the suturing process. However, structure utilized to create this feature may interfere with visibility in some prior art designs.

Kinks and cross over of the holder sutures increases the force needed to pull the holder sutures free after valve attachment. Pulling with a large force on the holder to release the valve after attachment to the patient may cause paravalvular leakage.

Applying too much tension on the holder sutures may cause a break in the holder suture. If the holder suture break occurs in an undesirable location, a suture remnant could be left in the patient when the physician subsequently cuts the holder suture to release the valve from the holder.

Commercial examples of heart valves include the Medtronic Mosaic® and Hanckock® II Aortic valves. Commercially available holder systems include the Cinch™ Advanced Implant System available from Medtronic of Minneapolis, Minn. Holders and packaging for heart valves are disclosed in U.S. Pat. Nos. 4,211,325; 4,865,600; 5,476,510; 5,716,401; 6,126,007; 6,338,740; 6,409,758; 6,558,418; 6,702,852; 6,736,845; 6,964,682; 6,966,925 and published U.S. patent application Ser. Nos. 2002-0082686-A1, 2003-0125805-A1; 2004-0138741-A1, 2004-0024451-A1; 2004-0148018-A1; and GB publication Nos. 2,108,393 and 2,011,259.

SUMMARY

Accordingly the present invention is directed to a valve holder that is removably attached to the prosthetic valve in a fashion that enhances visibility and accessibility during implantation of the heart valve in the patient.

In another aspect, the present invention comprises a valve holder having a suture path to reduce the likelihood of suture entanglement during attachment to the patient.

In another aspect, the present invention comprises a valve holder apparatus and method of attachment to reduce the likelihood of a suture remnant left in the patient.

In another aspect, the present invention comprises a method and apparatus to make the holder removal easier after insertion and attachment to the patient to prevent damage to the attachment between the valve and the patient.

The present invention provides an apparatus and method for use of a holder for securing a prosthetic heart valve while attaching the valve to the patient. More specifically, the present invention comprises an apparatus for holding a heart valve having small feet adapted to engage the heart valve at the inner portion of sewing ring. The small feet on the inner portion of the sewing ring provide unobstructed visibility of and access to the outer portion of the sewing ring for attachment of the valve sutures thereon. The feet comprise multiple through holes to create separate suture paths to reduce kinking and cross over of the holder suture attaching the holder to the sewing ring. The present invention further comprises a plurality of spider-like legs extending radially inward from the small feet to a central hub. The central hub has a small hub diameter to provide visibility and access between the hub and the sewing ring for observing and irrigating the valve during attachment to the patient. The hub comprising a winch-type suture gather module connected to a plurality of holder sutures. The holder sutures connect the valve to the holder by a first end on the hub and extending along a respective leg to pass through the sewing ring and engage two adjacent commissure posts and return through the sewing ring where a second end is tied to an adjacent leg. The gather module winds the holder sutures on the hub. The holder sutures bear against the valve commissure posts causing a deflection of the posts radially inward toward the axis of the valve to surround and contain the valve outlet. The gather module may be adapted to limit travel of the commissure post ends to prevent damage by touching the tips of the commissure posts together and limit the tension applied to the holder suture to prevent breakage. A break edge in the suture path is designed to cause unintentional suture breakage at a predetermined, highly desirable location. An unintentional break in the suture at a predetermined location can prevent a suture remnant when the physician subsequently cuts the holder suture to release the valve from the holder.

In one aspect the present invention provides a holder for a prosthetic heart valve having an unobstructed valve connection portion on the sewing ring.

In one aspect the present invention provides a holder for a prosthetic heart valve having a plurality of small feet on the inner portion of the sewing ring.

In one aspect the present invention provides a holder for a prosthetic heart valve having a viewing and access portal for observing and irrigating the inner surface of the valve during attachment.

In one aspect the present invention provides a holder for a prosthetic heart valve having a suture path for the holder suture on the inner portion of the sewing ring.

In one aspect the present invention provides an apparatus and method for attaching the holder to the valve to prevent kinking and cross over in the holder suture.

In one aspect the present invention provides a pre-configured break point for the holder.

In one aspect the present invention provides a holder for a prosthetic heart valve having a knot anchor spaced from the sewing ring to avoid entangling the holder suture knot with the valve suture.

In one aspect the present invention provides a holder for a prosthetic heart valve having a torque limiting mechanism on the commissure post gather module to prevent holder suture breakage and damage to the stent, commissure posts or biocompatible covering.

In one aspect the present invention provides a holder for a prosthetic heart valve having a wind up style commissure post gather module.

In one aspect the present invention provides a holder for a prosthetic heart valve having a rotary winch type commissure post gather module.

In another aspect the present invention provides a holder for a prosthetic heart valve having a gather module with an anti-reverse clutch.

In another aspect the present invention avoids suture remnants by providing a holder for a prosthetic heart valve having a predictable holder suture break point.

In one aspect the present invention provides a holder for a prosthetic heart valve having a holder suture path spaced from the valve suture area used to attach the valve to the patient.

In one aspect the present invention provides a holder for a prosthetic heart valve having a holder suture path designed to prevent kinking and cross over.

In another aspect, the present invention reduces the release force needed to pull the holder sutures free after attachment.

In another aspect, the present invention provides a kink free and cross over free path for the holder suture.

In another aspect, the present invention provides a holder for a prosthetic heart valve having a tension-balanced anti-reverse post gather module.

In another aspect, the present invention provides a holder for a prosthetic heart valve having a holder suture cut point to remove the holder suture from the commissure posts by cutting the suture and pulling the holder away to unthread the holder suture from the commissure posts.

In another aspect, the present invention provides a holder for a prosthetic heart valve having a low profile for maneuvering the valve into attachment position.

In another aspect, the present invention provides a holder for a prosthetic heart valve having a foot on the sewing ring adjacent each valve commissure post.

In another aspect, the present invention provides a holder for a prosthetic heart valve having a post gather module that holds the posts in a retracted state after removal of the handle.

In another aspect the present invention provides an apparatus requiring a low and consistent ratcheting torque force on the winch to tension the holder sutures for drawing in the commissure posts.

DESCRIPTION OF THE DRAWINGS

Some of the drawings omit portions of the valve assembly (e.g. portions constructed from tissue) for purposes of emphasizing other aspects of the invention such as details of the holder assembly.

DETAILED DESCRIPTION

The present invention is an improved apparatus for holding and maneuvering a valve during preparation and attachment to a patient. The present invention is adapted to provide increased visibility and accessibility of the prosthetic valve and the sewing ring during attachment. The present invention is used most effectively with mitral valves having commissure posts on the distally held outflow side of the valve structure but may be used with other valve configurations. The present invention is adapted to bend or deflect the commissure posts inward at the tips by limiting the tension on the holder sutures applied to deflect the commissure post and limiting the travel of the tips of the commissure posts. The holder sutures running across the valve outlet help resist damage to the bioprosthetic valve tissue by blocking the surgeon from looping the valve attachment sutures around the valve commissure posts. These bioprosthetic valve commissure posts are not visible during a mitral valve replacement surgery. The present invention further holds the commissure posts in the inward deflected position to prevent the commissure posts from the being damaged or entangled in the attachment sutures stitched between the patient and the sewing ring. The commissure posts are held in the deflected position even after handle removal and during tightening of the attachment sutures. The present invention provides an engineered break point for the holder sutures to avoid remnants left in the patient.

Figure 1:
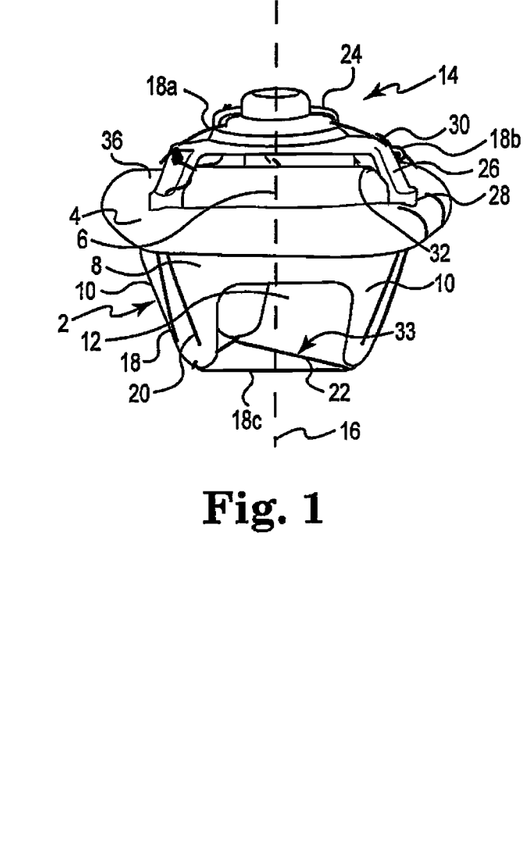
FIG. 1 is a perspective view of the present invention mounted on a prosthetic valve.

With reference to FIG. 1, present invention is illustrated as a valve holder 14 on a mitral valve 2. The mitral valve embodiment is discussed for illustrative purposes. The mitral valve version has a sewing ring 4 on the inlet 6 and a stent 8 comprising a plurality of commissure posts 10 surrounding the outlet 12 of the valve 2. The commissure posts 10 are connected to the sewing ring 4. The sewing ring 4 and stent 8 are covered by a biocompatible fabric 36. The valve 2 and valve holder 14 have a common axis 16. The valve holder 14 is attached with a first holder suture 18, second holder suture 20 and third holder suture 22. The central hub 24 has legs 26 and each leg 26 has a foot 28 on the sewing ring 4.

Surgeons typically use a green or white colored suture to stitch the biocompatible fabric 36 to the patient. Preferably, the sutures 18, 20, and 22 are not green or white. For example, they may be green. Optionally, the sutures 18, 20, 22 may be fluorescent, iridescent, opaque, phosphorescent or combinations thereof to avoid confusion with the implantation sutures.

Each leg 26 further has a knee 30 bent at an angle 32 greater than 90 degrees to extend the leg 26 axially downward to engage the sewing ring 4 at the foot 28. The central hub 24 is spaced axially from the sewing ring 4 to provide visibility and accessibility between the valve holder 14 and the sewing ring 4. Referring to holder suture 18 for illustration, each holder suture 18, 20, 22, has a first end 18a on the central hub 24 and a second end 18b tied to a leg 26. An intermediate portion 18c extends from the valve holder 14 to engage the valve 2.

As shown in FIG. 1, the preferred configuration is to have a leg 26 disposed in relation to each commissure post 10. The three commissure post 10 configuration of FIG. 1 results in the intermediate portions of the holder sutures 18, 20, 22 forming a triangular shaped holder suture mesh arrangement 33 adjacent the valve outlet 12.

Figure 2:
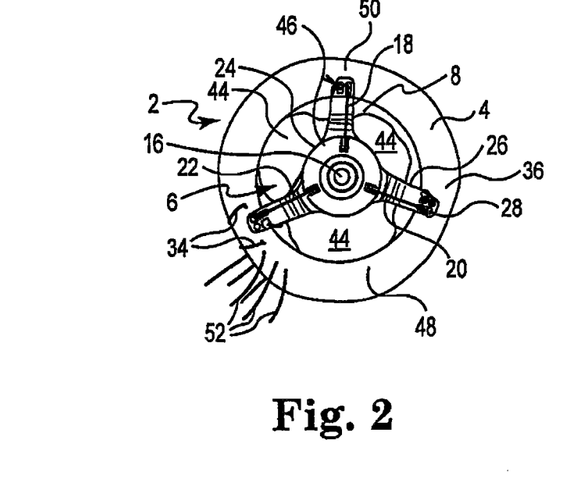
FIG. 2 is a top plan view of the present invention mounted on a prosthetic valve.

Referring to FIG. 2, the present invention is shown as viewed looking along the axis 16 of the valve 2. The central hub 24 is axially located with respect to the sewing ring 4. The sewing ring 4 is continuous and circumscribing the inlet 6 of the valve 2. The legs 26 extend radially from the central hub 24. A marker suture 34 is sewn onto the sewing ring to mark the position of the right fibrous trigone (not shown) during implantation. This marker suture 34 is a contrasting color, (possibly but not preferably green), to the holder sutures 18, 20, 22 (e.g. which may be black). The marker suture 34 is also preferably not green or white and contrast with both the sutures 18, 20, 22 and the color of the fabric 36 (typically white). The holder sutures 18, 20, 22 are a contrasting color to the valve sutures 52 used to attach the valve to the patient. Valve sutures 52 are may be an alternating white and green color. These color contrasts are also distinguishable from the white fabric 36 covering the stent 8. When directed towards the right fibrous trigone, the marker suture 34 on the mitral valve 2 aligns the widest inter-commissural space between the commissure posts 10 with the patient's left ventricular outflow tract in order to avoid potential stent post obstruction.

Continuing to refer to FIG. 2, the plurality of holder sutures 18, 20, 22 extend from the central hub 24 along a respective leg 26 to engage and hold the sewing ring 4 removably attached to the foot 28 on each respective leg 26. A plurality of visibility and access portals 44 are formed between adjacent legs 26 and the sewing ring 4. The valve leaflets may be viewed from adjacent the top 46 of the hub 24 through the visibility portals 44.

Continuing to refer to FIG. 2, each foot 28 is on an inner portion 48 of the sewing ring 4. An outer portion 50 of the sewing ring 4 is unobstructed by the valve holder 14. The outer portion 50 is connected to the patient (not shown) by valve sutures 52 on the sewing ring 4. The valve sutures 52 are placed sequentially around the sewing ring 4 spaced from the holder sutures 18, 20, 22 to securely attach the valve 2.

Figure 3:
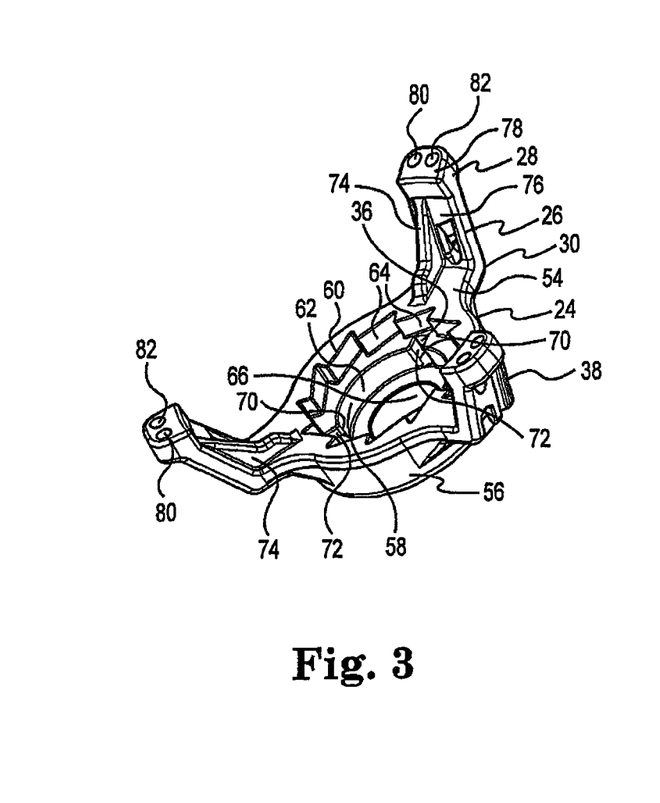
FIG. 3 is a perspective bottom view of the valve holder with the ratchet removed.

Referring to FIG. 3, the central hub 24 has a bottom 54 and an outer wall 56. A spool chamber 58 is formed in the central hub 24. The central hub 24 has a winch opening 60 and an inner surface 62 surrounding the spool chamber 58. A plurality of ratchet teeth 64 are formed in the spool chamber 58. The ratchet teeth 64 are disposed around the perimeter of the winch opening 60.

Continuing to refer to FIG. 3, the inner surface 62 further co a circular channel 66, a break edge 70 adjacent each leg 26. The circular channel 66 is formed adjacent the handle opening 68. The break edge 70 is on the inner surface 62 at the spool opening 72 (FIG. 9) to each the suture outlet (FIG. 4).

The leg 26 comprises a knee 30 and a foot 28. A strut 74 is formed on the bottom 76 of each leg 26 to structurally support the leg 26 behind the suture slot 38. The foot 28 comprises a bottom 78, an exit hole 80 and an entrance hole 82. The exit hole 80 and entrance hole 82 are spaced from each other. The spaced apart exit hole 80 and entrance hole 82 prevent holder suture entanglement.

Figure 4:
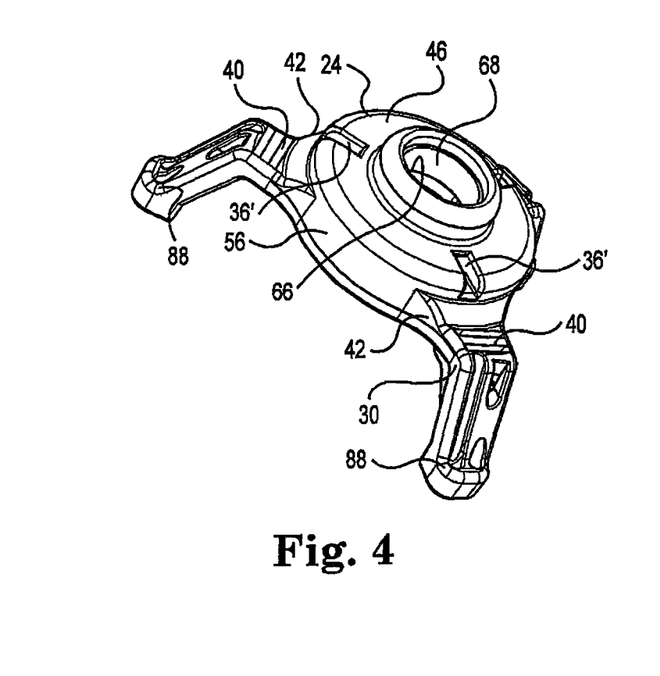
FIG. 4 is a perspective top view of the valve older with the ratchet removed.

Referring to FIG. 4, the central hub 24 comprises a top 46, an outer wall 56 and a spool chamber 58. The legs 26 have a first end 42 on the central hub 24 adjacent a respective suture outlet. A cutting flat 40 is formed on each leg 26 intermediate the knee 30 and the first end 42. The foot 28 is on the second end 120 (FIG. 7 or see FIG. 4) of the leg 26. The foot 28 has a top 88.

Figure 5:
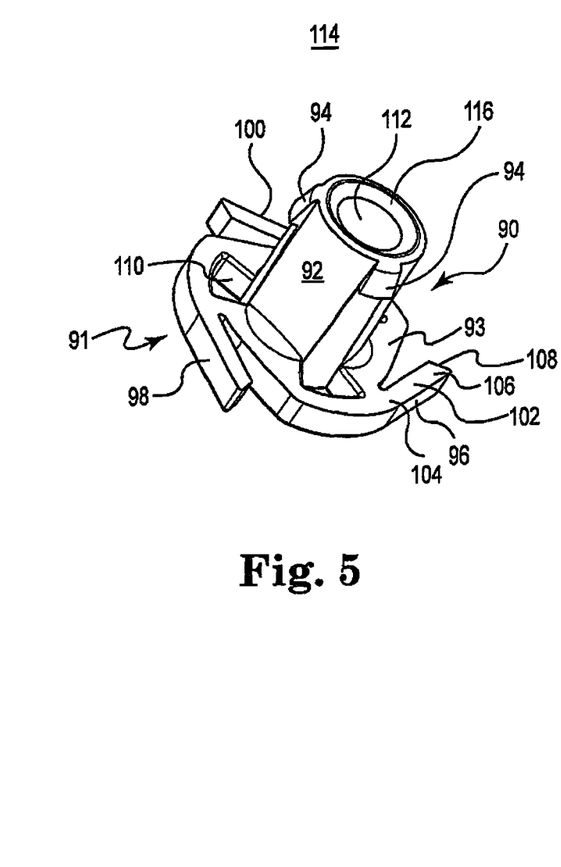
FIG. 5 is a perspective top view of the ratchet removed from the valve holder of FIG. 3.

Referring to FIG. 5, the handle adapter 114 is axially connected to the proximal end 112 of the spool 92. The handle adapter 114 may be fixed to the spool 92 by welding or epoxy or the like. In an alternate embodiment, the handle adapter 114 has a releasable union 116 thereon. The releasable union 116 is connected to the spool 92. The releasable union 116 is adapted to rotatably release the spool 92 if the rotating torque exceeds a predetermined torque limit. If the handle adapter 114 rotatably releases the spool 92, the handle adapter 112 will turn freely in the spool 92. The releasable union 116 may also be adapted with a one way connector (not shown) to facilitate handle (not shown) removal. The releasable union 116 may be a torque limiting clutch, an adhesive applied with a determinative release property or a plurality of molded tabs having a predetermined shear strength between the handle adapter 114 and the spool 92.

Figure 6:
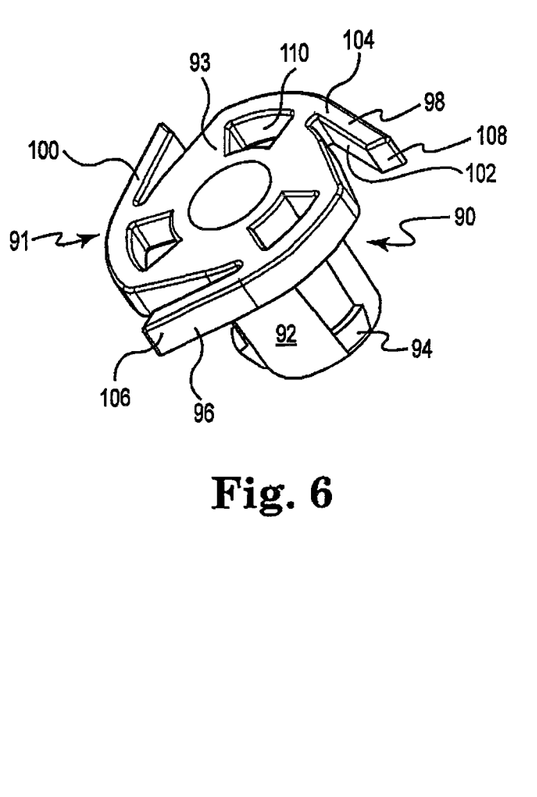
FIG. 6 is a perspective top view of the ratchet removed from the valve holder of FIG. 4.

Referring to FIGS. 5 and 6, the ratchet 90 has a spool 92, an end flange 93, a plurality of snap fit tabs 94 and an anti-reverse device 91. The spool 92 is on the end flange 93. The anti-reverse device 91 is on the end flange 93. The anti-reverse device 91 comprises a first pawl 96, second pawl 98 and third pawl 100 on the end flange 93. Each pawl 96, 98, 100 comprises a flexible link 102 having a first end 104 on the ratchet 90 and an engagement member 108 on a second end 106. The flexible link 102 is made of a resilient material to urge the engagement member 108 radially outward from the spool 92. A plurality of suture holes 110 are formed in the ratchet 90 for attaching a first end of a holder suture 18, 20, 22.

Continuing to refer to FIGS. 4, 5 and 6, the ratchet 90 is rotatably mounted in the spool chamber 58. The snap fit tabs 94 have an interference snap fit with the central hub 24 by inserting the ratchet 90 in the spool chamber 58 by snapping into the channel 66 to hold the ratchet 90 in the spool chamber 58. The snap fit tabs 94 slide in the channel 66 around the perimeter of the spool chamber 58 when the ratchet 90 rotates with respect to the central hub 24.

Figure 7:
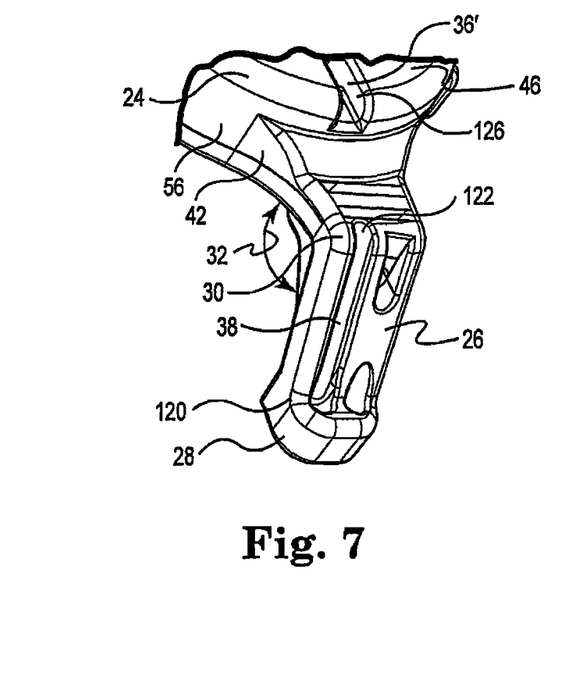
FIG. 7 is a perspective top view of a leg of the valve holder of FIG. 4.

Referring to FIG. 7, each leg 26 comprises a first end 42, a knee 30 and a second end 120. The first end 42 is attached to and extends from the outer wall 56 adjacent the bottom 54 of the central hub 24. The second end 120 is thereby radially spaced from the central hub 24. The knee 30 is formed at an angle 32 to hold the foot 28 axially spaced from the central hub 24. The knee 30 has a radiused top 122 adjacent the suture slot 38. The suture outlet opens from the outer wall 56 at leg opening 126. A suture outlet is adjacent the first end 42 of each leg 26.

Figure 8:
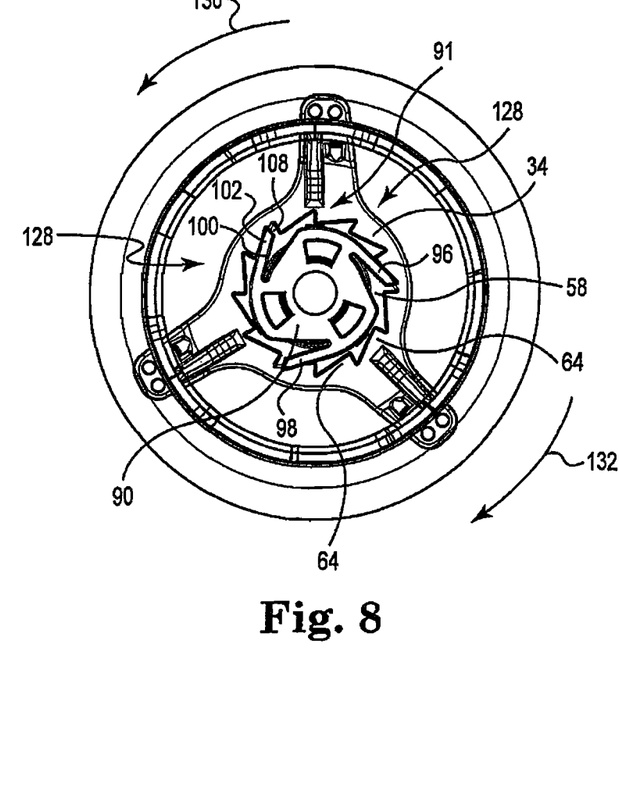
FIG. 8 is a bottom plan view of the valve holder with the ratchet installed in the hub.

Referring to FIG. 8, the gather module 128 comprises the ratchet 90 rotatably mounted in the spool chamber 58 (FIG. 3) of the central hub 24. The anti-reverse device 91 in the preferred embodiment is mounted on the ratchet 90 and adapted to engage the central hub 24. The anti-reverse device 91 has the plurality of ratchet teeth 64 formed in the central hub 24 adapted to engage each of the pawls 96, 98, 100. The flexible link 102 allows the engagement member 108 to slide over the ratchet teeth 64 as the ratchet 90 is rotated in a first direction 130. The teeth 64 engage the pawls when the spool 92 is turned in the second direction 132. The plurality of pawls 96, 98, 100 engaging a plurality of ratchet teeth 64 simultaneously balances the tension on the ratchet 90 to resist breaking. The anti-reverse device 91 may alternately be an anti-reverse bearing, ratchet mechanism or unidirectional clutch or other mechanical rotation direction limiting device.

Figure 9:
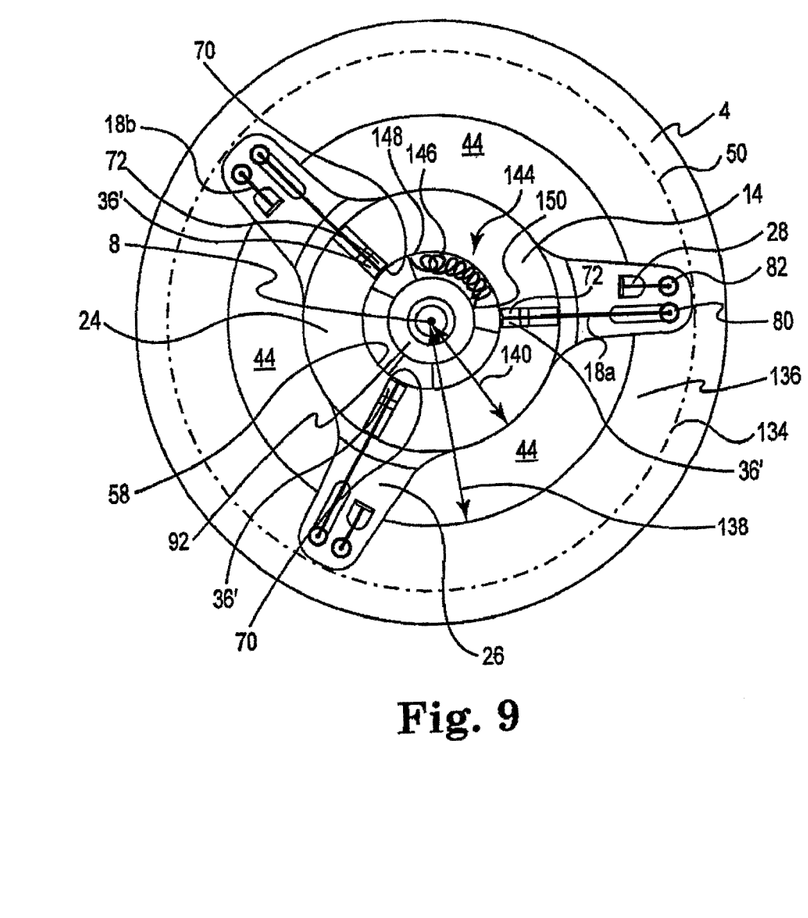
FIG. 9 is a top plan view of the present invention on a sewing ring.

Referring to FIG. 9, the valve holder 14 is on the sewing ring 4. Each foot 28 is small to fit between the sewing ring centerline 134 and the inner perimeter 136. The inner perimeter 136 has a radius 138. The central hub 24 has a hub radius 140. The outer portion 50 of the sewing ring 4 is defined approximately between the centerline 134 and the outer perimeter 142 of the sewing ring 4.

Continuing to refer to FIG. 9, the top 46 of the central hub 24 is cut away to illustrate the spool 92 in the spool chamber 58 and the suture outlets. The suture outlets are adjacent a respective leg 26. Each suture outlet has a spool opening 72 adjacent the spool chamber 58 and a leg opening 126 adjacent the leg 26. The spool opening 72 has a break edge 70 at its interface with the inner surface 62. It should be understood the holder sutures 18, 22, 24 are directed to bear against the break edge 70 by the radial alignment of the first end 18a (FIG. 10) on each leg 26. This radial alignment forces the holder suture 18 to bend over the break edge 70 to tangentially wind onto the spool 92. Bending over the break edge 70 forms a pre-engineered break point for the holder sutures in the event the ratchet 90 is wound too tight or excess tension is otherwise applied to the intermediate portion of the holder suture 18, 20, 22.

Figure 10:
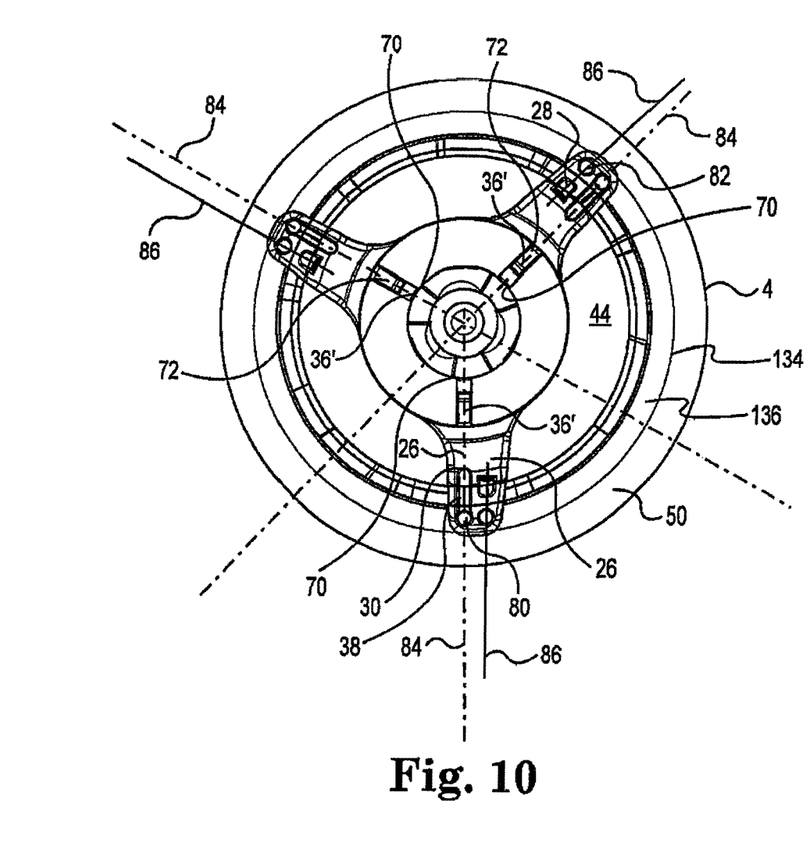
FIG. 10 is a top outline view of the present invention showing suture paths.

Continuing to refer to FIG. 9 the first holder suture 18 is illustrated for descriptive purposes. The first holder suture 18 has a first end 18a on the spool. The first end 18a extends along a first holder suture path 84 defined between the break edge 70 to the exit hole 80. Holder suture 18 has a second end 18b on an adjacent leg 26 in second suture path 86. The second end 18b is tied to the suture anchor of the adjacent leg 26.

Continuing to refer to FIG. 9, a rotation limiter 144 is attached to the central hub 24 and extended to attach to the spool 92. The rotation limiter 144 is a means for limiting how much of the holder suture 18, 20, 22 is wound onto the spool 92. The rotation limiter 144 is shown as cord 146 with a slack length, a first end 150 on the central hub 24 and a second end 148 on the spool 92. As the spool 92 is turned to wind up the holder sutures 18, 20, 22 (FIG. 3), the cord 146 is also wound on the spool 92. The length of the cord 146 is determined to allow a predetermined angular displacement of the spool 92 and a corresponding linear gathering of the holder suture 18, 20, 22 onto the spool 92 to reduce the length of the intermediate portion of each holder suture. The reduced length of the intermediate portion of the holder sutures tensions the holder sutures to bear against the commissure posts 10 (FIG. 1) to displace the tips 34 radially inward. The rotation limiter 144 limits the travel of the commissure posts 10 to prevent damage by the commissure posts 10 touching each other. When the slack is gathered on the spool 92, the spool is connected to the central hub 24 by the cord 146 and the spool 92 cannot rotate further.

The rotation limiter 144 may alternately be a watch spring having a first end on the central hub and a second end on the ratchet 90. The rotation limiter 144 may in an alternative embodiment be a threaded connection (not shown) between the hub 24 and the ratchet 90. In one alternate embodiment, rotation of the ratchet 90 causes a linear translation along the threaded connection (not shown). The linear translation is limited to allow a predetermined rotation travel of the ratchet 90. In another alternate embodiment of the rotation limiter 144, the threaded connection (not shown) may be adapted to limit the rotational travel of the ratchet 90. In yet another embodiment of the rotation limiter 144, a pin feature (not shown) on the spool 92 can be adapted to travel in a corresponding slot (not shown) in the central hub 24. Rotation of the spool 92 causes the ratchet 90 to physically stop at a prescribed limit when the pin (not shown) bears against a stop (not shown) in the slot (not shown).

Referring to FIG. 10, the first holder suture path 84 is axially aligned. The first suture path 84 comprises the break edge 70, the suture outlet, the knee 30, the suture slot 38 and the exit hole 80 on a respective leg 26. The second suture path 86 is likewise formed on each leg. The second suture path 86 comprises the entrance hole 82 and the suture anchor. The first suture path 84 is radially aligned with respect to the axis 16.

Figure 11:
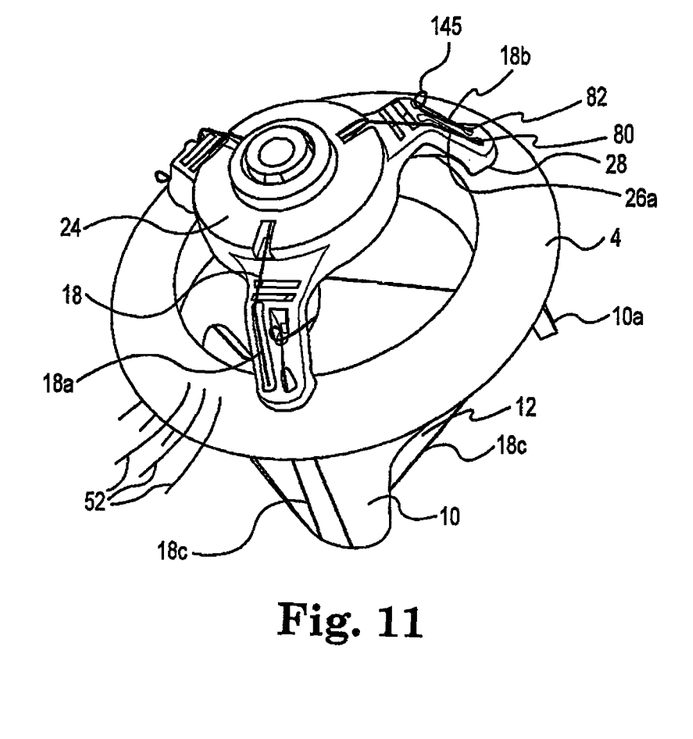
FIG. 11 is a top perspective view of the present invention attached to a prosthetic valve.

Referring to FIG. 11, the present invention is shown in perspective with the valve attached. The first holder suture 18 has a first end 18a tied to the ratchet 90 in the spool chamber 58 and extending along the first suture path 84 to engage the valve 2 at the sewing ring 4 adjacent the respective foot 28. The first holder suture 18 has an intermediate portion 18c which penetrates through the sewing ring 4 and extends along the commissure post 10 proximate to the respective foot 28. The intermediate portion 18c engages the commissure post 10 at the tip and extends across the valve outlet 12 to engage the tip of an adjacent commissure post 10a. The intermediate portion 18b extends up along the outside of the adjacent commissure post 10a to engage the sewing ring 4 proximate to the adjacent commissure post 10a.

The first holder suture 18 has second end 18b that extends along the second suture path 86 on the adjacent leg 26a. The second end 18b passes through entrance hole 82 from the bottom 78 of the foot 28 on the adjacent leg 26a. Knot 145 in second end 18b is tied to the suture anchor on the adjacent leg 26a.

Figure 12:
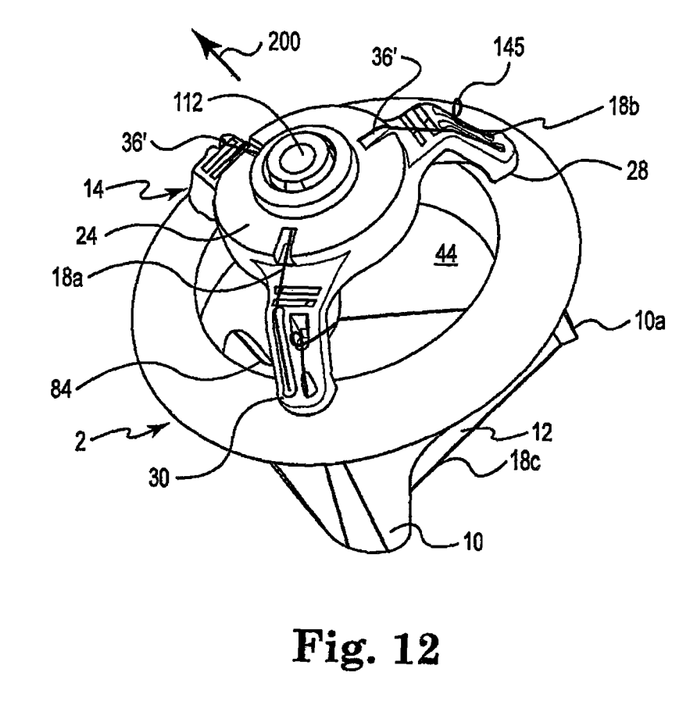
FIG. 12 is the view in FIG. 11 with the holder sutures cut for separation of the holder and the valve.

Referring to FIG. 12, after attachment to the patient, the first end 18a is cut at the cutting flat 40. A release force 200 is applied axially to the valve holder 14 to separate the valve holder 14 from the valve 2. Referring to the first holder suture 18 for illustration, the release force 200 causes the first holder suture 18 to unthread from the valve 2 by pulling on the second end 18b. The second end 18b pulls the intermediate portion 18c and the attached portion of the first end 18a from the valve 2 in one piece. The first end 18a remains attached to the hub 24. The attached portion of the first end 18a is pulled along the first suture path 84 through the exit hole 80 and continues to unthread by following the passageway of the intermediate portion 18c until the first holder suture 18 is separated from the valve 2.

The holder sutures 18, 20, 22 of the present invention provide an improved performance over the prior art. The torque 118 required to wind the spool 92 and deflect the commissure posts 10 is less than the prior art because the holder sutures do not bind on themselves or other holder sutures. The release force 200 required to pull the holder 14 free of the valve 2 and unthread the holder sutures 18, 20, 22 is less than with prior art designs. The holder sutures 18, 20, 22 do not kink as they are tensioned and pulled over the knee 30 having the obtuse bend angle 32 and the radiused top 122 adjacent the suture slot 38. The first and second suture paths 84, 86 spaced from each other separate the holder sutures 18, 20, 22 to prevent binding. The separate holes 80, 82 in each foot 28 prevent the holder suture from binding on itself and the other holder sutures when the holder suture is pulled free from the valve 2. Lastly, the suture anchor spaced from the sewing ring 4 prevents entanglement with the valve sutures 52.

In use, the valve 2 is attached to the valve holder 14 which is held by a handle (not shown) attached to the handle adapter 112. The handle is turned, turning the handle adapter 112, with respect to the holder 14, to draw the tips of the commissure posts 10 in around the outlet 12 of the valve 2. The valve 2 is rotated to orient the marker suture 34 with respect to the patient's anatomy for optimum performance. Valve sutures 52 are connected to the outer portion 50 of the sewing ring 4 and to the annulus of the patient's valve. The handle (not shown) is removed to tighten and tie off the valve sutures 52. The holder sutures 18, 20, 22 are cut at the cutting flat 40. The commissure posts 10 resiliently return to their configured shape and position extending parallel to the axis 16 and surrounding the outlet 12 of the valve 2. This snap back by the commissure posts 10 begins to draw the holder sutures 18, 20, 22 out from the engagement position holding the valve holder 14 to the valve 2.

The valve holder 14 is pulled axially from the valve 2 to remove the holder and holder sutures 18, 20, 22 from the patient. It should be understood, the holder sutures 18, 20, 22 are connected to the valve holder 14 at the respective second end tied to the suture anchor of a respective leg 26. The holder sutures 18, 20, 22 must pull free of the valve 2 by unthreading the intermediate portion 18c. The kink free suture paths 84, 86 minimize the release force 200 required to pull the holder sutures 18, 20, 22 free. The holder sutures 18, 20, 22 pull free and are removed with the valve holder 14. The first end 18a of each holder suture 18 remains connected to the central hub 24. The second end 18b of each holder suture remains attached to the suture anchor. The intermediate portion of the holder suture is attached to the second end 18b and is pulled through the exit hole 80 and out of the sewing ring 4 adjacent the exit hole 80. The intermediate portions of the holder suture 18, 20, 22 are further pulled out of the tips of the two adjacent commissure posts 10 and out of the sewing ring 4 adjacent the entrance hole 82.

Example 1

Figure 13:
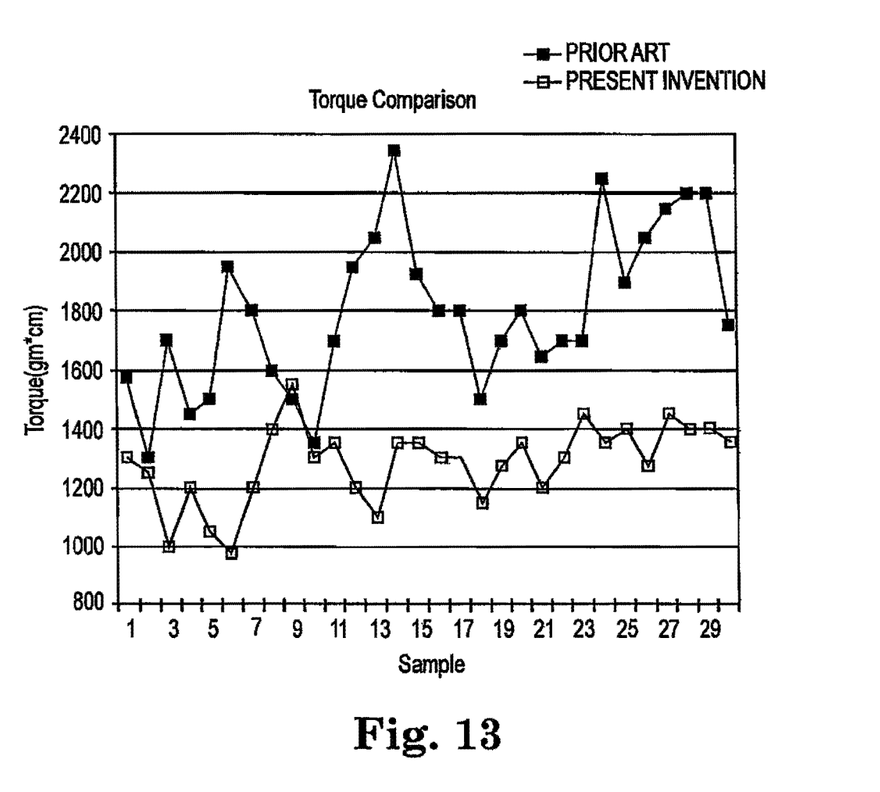
FIG. 13 is a chart from a comparison study of torque required on the handle adapter to turn the spool to gather the holder sutures and deflect the commissure posts radially inward at the valve outlet.

The torque 118 required to wind the holder sutures 18, 20, 22 onto the spool 92 is reduced by the design and the improved suture paths 84, 86. The reduced torque 118 translates to lower tension on the holder sutures. Lowering the tension of the holder sutures 18, 20, 22 reduces the chance that the holder sutures will break during deflection of the commissure posts. FIG. 13 illustrates a comparison study of torque 118 required on the handle adapter 112 to turn the spool 92 to gather the holder sutures and deflect the commissure posts 10 radially inward at the valve outlet 12. Torque 118 is reduced by an average of more than 25% over the prior art tested.

TABLE 1

FIG. 13 Summary Analysis

| Sample size N = 30 | Prior Art Torque (gm * cm) | Present Invention Torque (gm * cm) |
|---|---|---|
| Mean | 1795 | 1284 |
| Std. Deviation | 272 | 134 |

Example 2

Figure 14:
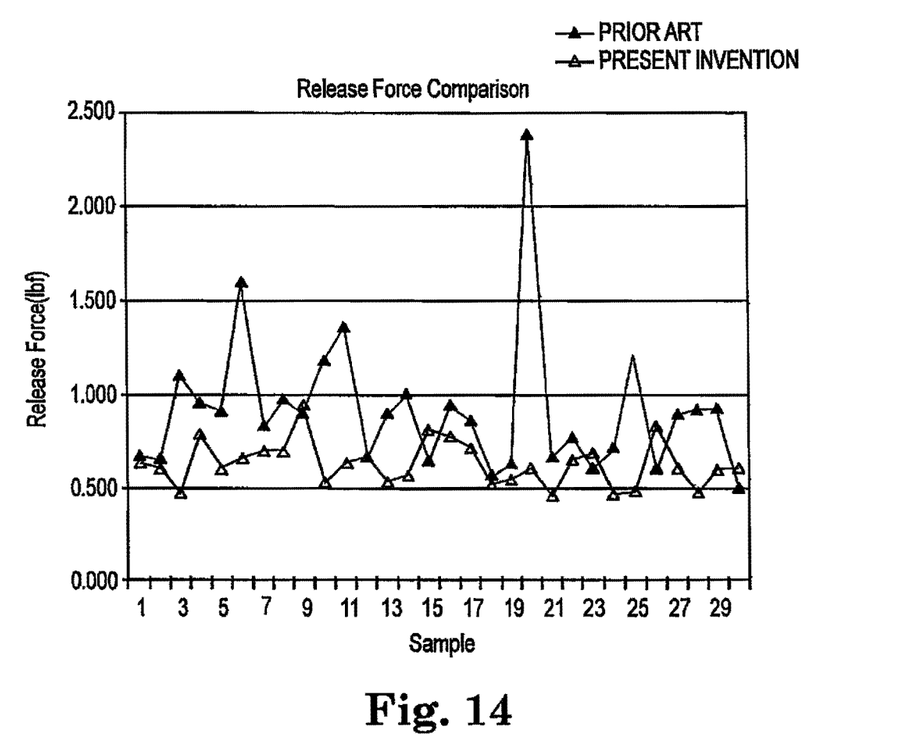
FIG. 14 is a chart illustrating the release force required to pull the holder sutures free of the valve comparing a prior art holder and the present invention.

The release force 200 (FIG. 12) to remove the valve holder 14 from the valve 2 is an improved, lower release force 200 than prior art designs. The lower release force 200 reduces the chance of pulling the valve sutures 52 loose. FIG. 14 illustrates the release force 200 required to pull the holder sutures 18, 20, 22 free of the valve 2 comparing the prior art holder and the present invention. The reduced release force 200 (average 30% lower) results in less pull on the valve sutures 52 insuring the integrity of the attachment of the valve 2 to the patient.

TABLE 2

FIG. 14 Summary Analysis

|  | Prior Art Release Force (lbf) | Present Invention Release Force (lbf) |
|---|---|---|
| Mean | 1795 | 1284 |
| Std. Deviation | 272 | 134 |

Figure 15:
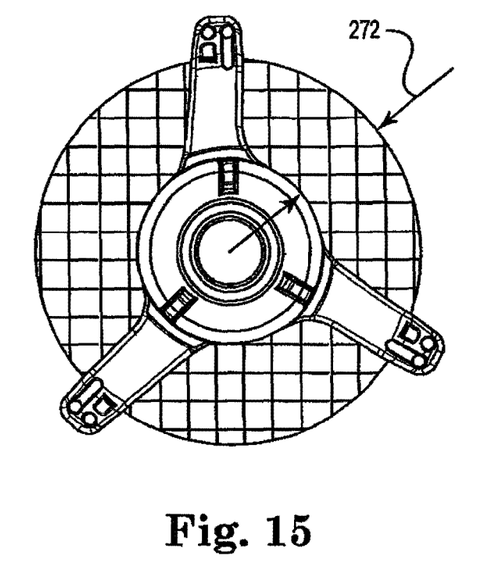
FIG. 15 is a schematic illustration of an aspect of the present invention.
Figure 16:
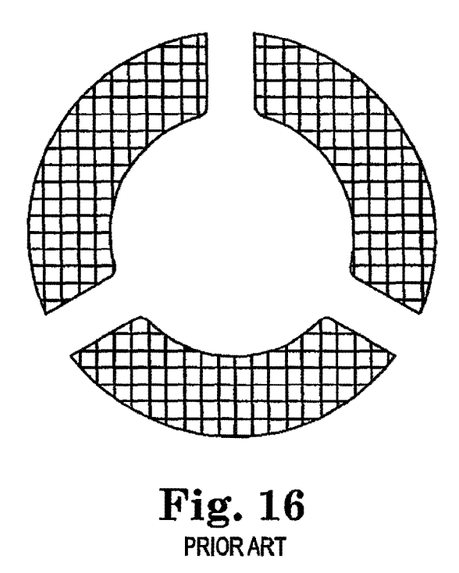
FIG. 16 is a schematic illustration showing a prior art visibility or aspect ratio.

The present invention also provides for increased visibility or access over prior art holders. This is believed to increase visibility during use of the holder as well as access to the site for substances such as fluids. This may be accomplished by reducing the structure of the holder that blocks vision. FIG. 15 schematically illustrates a preferred visibility or access ratio relative to the prior art. FIG. 16 schematically illustrates the visibility or access ratio of a prior art mitral valve holder.

As can be seen in FIGS. 16 and 15, the visibility ratio or access ratio is the exposed cross sectional area bounded by the inner diameter or radii of the sewing ring of the valve minus the area of any portion of the holder that would block visibility along the longitudinal axis of the valve or holder. See the arrows 272.

The visibility or access ratio of the prior art device is 0.56. The visibility or access ratio of the example of the present invention is 0.62. It should be noted that the present invention includes any holder that afford a visibility or access ratio greater than 0.56, more preferably greater than about 0.58, more preferably greater than 0.6 and more preferably, greater than about 0.62.

The following example illustrates a calculation for the visibility or access ratio:

The sample of the present invention is the Cinch Mitral Holder Size 33 (available from Medtronic, Inc. of Minnesota) Size 33 (ID=30 mm). The prior art is the Size 33 (ID=33 mm) mitral valve holder previously sold by Medtronic.

By accounting for the area blocked by the legs of the holders the ratios are calculated as follows:

| Open Area Old = 0.613 | v. | Open Area New = 0.681 |
|---|---|---|
| Total Area Old = 1.096 |  | Total Area New = 1.096 |

Visibility or Access Ratio for Prior Art = 0.56  Present Invention = 0.62

Without accounting for the legs of the holders, the ratios are accounted for as follows:

| Open Area Old = 0.711 | v. | Open Area New = 0.850 |
|---|---|---|
| Total Area Old = 1.096 |  | Total Area New = 1.096 |
| Ratio: 0.65 |  | Ratio = 0.78 |

As can be seen above, the present invention results in an increase in the open area of 11%.

All patents, patent applications, publications and journal articles mentioned herein are expressly incorporated by reference.

Although the invention has been described above in connection with particular embodiments and examples, it will be appreciated by those skilled art that the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A method of attaching a valve holder to a prosthetic heart valve, the heart valve having an axis, an outlet and an inlet, a sewing ring on the valve adjacent the inlet, the sewing ring having an inner portion and an inside diameter, a stent on the valve adjacent the outlet, the stent having a plurality of commissure posts adjacent the outlet end, the method comprising:
   receiving a holder with a small central hub, a plurality of radially extending legs on the central hub, each leg having a small foot on the inner portion of the sewing ring and a rotatable spool mounted in the central hub;
   attaching a holder suture onto the spool for each one of the plurality of legs, the holder suture attached at a first end;
   wherein the holder defines:
      a first suture path for the first end of each holder suture, the first holder suture paths comprising suture outlet in the central hub adjacent each one of the plurality of legs, a suture slot in the respective leg, and an exit hole in the small foot,
      a second suture path for each holder suture, the second suture paths comprising an entrance hole in the small foot on each leg and a suture anchor spaced from the foot on each respective leg;
   extending the first end of each holder suture from the spool along a respective first suture path;
   attaching the holder to the valve by:
      engaging the sewing ring at the inner portion of the sewing ring adjacent the first suture path,
      threading each of the plurality of holder sutures through a commissure post adjacent the first suture path and an adjacent one of the plurality of commissure posts, engaging the sewing ring a second time with each holder suture adjacent the adjoining commissure post, and extending a second end of each holder suture along the second suture path on the leg adjacent the adjoining one of the plurality of commissure posts and tying each holder suture to a suture anchor;

attaching the valve to a patient by valve sutures on the sewing ring, the valve sutures spaced from the holder sutures; and cutting the holder sutures adjacent the central hub and pulling with a release force along the axis of the valve to remove the holder from the valve, the holder sutures remaining connected at the suture anchors.

2. The method of claim 1 wherein the holder sutures are a first color, the valve sutures are a second color, the first color distinguishable from the second color whereby the holder suture to be cut to remove the holder from the valve is identifiable by color.

3. The method of claim 2 further comprising the step before the step of providing a holder, the step comprising marking the location of the right fibrous trigone by attaching a marker suture to the sewing ring adjacent the right fibrous trigone, the marker suture having a third color, the third color distinguishable from the first and second colored sutures.

4. The method of claim 1, wherein the step of attaching the valve to a patient further includes:

viewing a target site through a viewing portal between the central hub and the sewing ring.

5. The method of claim 4, wherein the viewing portal is defined by a maximum outer diameter of the central hub being less than the inside diameter of the sewing ring.

6. The method of claim 5, wherein the inside diameter of the sewing ring is at least twice as large as the maximum outer diameter of the central hub.

7. The method of claim 1, wherein the holder forms a plurality ratchet teeth and the spool forms a plurality of pawls adapted to engage the ratchet teeth, and the method further including:

rotating the spool relative to the central hub in a first direction to draw the at least one of the posts radially inwardly;

wherein the pawls selectively engage the ratchet teeth to resist rotation of the spool relative to the central hub in a second direction opposite the first direction.

8. The method of claim 7, wherein the holder further includes a releasable union releasably attached to the spool, and further wherein the step of rotating the spool includes the releasable union disconnecting the spool relative to the central hub if an applied torque exceeds a pre-determined level.

9. The method of claim 7, wherein the step of attaching the holder to the valve includes attaching each holder suture to the spool.

10. The method of claim 9, wherein the step of rotating the spool includes winding each holder suture onto the spool.

11. The method of claim 10, wherein the step of rotating the spool includes shortening an effective length of the holder sutures to cause the holder sutures to bear against two adjacent commissure posts and draw the two adjacent commissure posts radially inward.

12. The method of claim 1, wherein the sewing ring provides an inlet side surface and further has an outside diameter and a centerline diameter, the inner portion comprising a surface region intermediate the inside diameter and the centerline diameter, wherein each small foot is positioned completely within and on the inner portion of the sewing ring.

13. The method of claim 12, wherein each leg further includes a knee defined by a fixed inside bend in the leg, the bend at an obtuse angle.

* * * * *